United States Patent
Riley et al.

(10) Patent No.: US 11,094,400 B2
(45) Date of Patent: *Aug. 17, 2021

(54) SYSTEM, METHOD AND APPARATUS FOR PROCESSING PATIENT INFORMATION AND FEEDBACK

(71) Applicant: TAPCLOUD LLC, Monterey, CA (US)

(72) Inventors: Thomas Patrick Riley, Glenview, IL (US); Steven Robert Grundy, Northbrook, IL (US); George J. Hayman, Jr., Oakbrook Terrace, IL (US); Mason Sheppard Levy, Chicago, IL (US); Kaitlin Diane Grundy, Northbrook, IL (US); Devin Henkel-Legare, Downers Grove, IL (US)

(73) Assignee: TapCloud LLC, Monterey, CA (US)

( * ) Notice: Subject to any disclaimer, the term of this patent is extended or adjusted under 35 U.S.C. 154(b) by 202 days.

This patent is subject to a terminal disclaimer.

(21) Appl. No.: 16/525,793

(22) Filed: Jul. 30, 2019

(65) Prior Publication Data

US 2019/0355446 A1 Nov. 21, 2019

Related U.S. Application Data

(63) Continuation of application No. 14/321,032, filed on Jul. 1, 2014, now Pat. No. 10,388,406.

(60) Provisional application No. 61/842,130, filed on Jul. 2, 2013.

(51) Int. Cl.
*G16H 10/20* (2018.01)

(52) U.S. Cl.
CPC ................... *G16H 10/20* (2018.01)

(58) Field of Classification Search
CPC ...... G06Q 50/22; G06Q 50/24; G06F 19/322; G06F 19/323–327; G06F 19/30; G06F 19/32; G06F 19/34; G06F 19/3418; G06F 19/36; G16H 10/00; G16H 10/60; G16H 20/00; G16H 50/00; G16H 50/30; G16H 80/00; G16H 10/20
USPC ........................................................ 705/2, 3
See application file for complete search history.

(56) References Cited

U.S. PATENT DOCUMENTS

| | | | |
|---|---|---|---|
| 6,383,135 B1 | 5/2002 | Chikovani | |
| 6,955,646 B2 | 10/2005 | Christ | |
| 8,818,788 B1 | 8/2014 | Mihalik | |
| 9,923,859 B1 * | 3/2018 | Soundararajan | ........ H04L 51/32 |
| 2007/0016451 A1 | 1/2007 | Tilson | |
| 2008/0071929 A1 | 3/2008 | Motte | |

(Continued)

OTHER PUBLICATIONS

U.S. Appl. No. 14/321,032, filed Jul. 1, 2014.

(Continued)

*Primary Examiner* — Jason S Tiedeman
(74) *Attorney, Agent, or Firm* — Barnes & Thornburg LLP

(57) ABSTRACT

An apparatus system and method for processing patient data pursuant to a monitoring period, wherein received patient feedback data is processed and structured to provide a selectable keyword cloud to a display. The keyword cloud may include a plurality of at least one of symptoms, complications and patient conditions, wherein the keyword cloud is structured by a processor for display in accordance with previous patient feedback data during at least part of the monitoring period.

21 Claims, 9 Drawing Sheets

(56) References Cited

U.S. PATENT DOCUMENTS

| | | |
|---|---|---|
| 2008/0146893 A1 | 6/2008 | Levendowski |
| 2008/0183500 A1 | 7/2008 | Banigan |
| 2010/0223068 A1 | 9/2010 | Von Schweber |
| 2010/0299155 A1 | 11/2010 | Findlay |
| 2011/0029873 A1 | 2/2011 | Eseanu |
| 2011/0231797 A1* | 9/2011 | Huhtala ............ G06F 3/017 |
| | | 715/811 |
| 2012/0167010 A1* | 6/2012 | Campbell .......... G06F 16/9535 |
| | | 715/825 |
| 2012/0290988 A1 | 11/2012 | Sun |
| 2013/0080348 A1 | 3/2013 | Pantaliano |
| 2013/0151589 A1* | 6/2013 | Eden ................ H04L 67/20 |
| | | 709/203 |
| 2013/0282404 A1 | 10/2013 | Janevski |
| 2014/0195531 A1* | 7/2014 | Diament ........... G06F 16/9024 |
| | | 707/736 |
| 2014/0282244 A1 | 9/2014 | Speer |
| 2015/0058320 A1 | 2/2015 | Zheng |

OTHER PUBLICATIONS

Microsoft Computer Dictionary, Fifth Edition (2002), 4 pages.
Dictionary of Computer and Internet Terms, Tenth Edition (2009), 5 pages.

\* cited by examiner tapcloud
BETTER INSIGHTS, BETTER OUTCOMES.

HOME   PROCEDURE MAPPING   MEDICATION MAPPING   PATIENTS   LOGOUT

PROCEDURE/COMPLICATIONS   COMPLICATION/SYMPTOMS   SYMPTOM/KEYWORDS

SYMPTOM/KEYWORDS — 202

EVERY SYMPTOM HAS CERTAIN KEYWORDS (OR PHRASES). USE THE DATA BELOW TO ADD OR REMOVE KEYWORDS FOR THIS SYMPTOM.

SYMPTOM: [PYREXIA : FEVER ▾]

ASSIGNED KEYWORDS — 203
- CAN'T GET OUT OF BED -
- CHILLS -
- CRAPPY -
- NO ENERGY -
- PERSPERATION -
- RUN DOWN -
- SWEATING -
- TIRED -
- WHOLE BODY ACHE -

UNASSIGNED KEYWORDS — 204
- ANXIOUS -
- BETTER -
- BLOCKED -
- BLUES -
- CALF PAIN -
- CAN'T CONCENTRATE -
- CAN'T MOVE -
- CAN'T SLEEP -
- CHEST TICKLE -
- CLAMMY HANDS -
- CONGESTED -
- CONSTIPATED -
- DEPRESSED -
- DIARRHEA -
- DISTENDED STOMACH -
- DOWN -
- DRY COUGH -
- EXHAUSTED -
- FART -
- FLATULENT -
- FLUSHED -
- FULL -

CREATE A KEYWORD — 204a

KEYWORD [          ]   [ADD]

*FIG. 2A* tapcloud
BETTER INSIGHTS. BETTER OUTCOMES.

HOME    PROCEDURE MAPPING    MEDICATION MAPPING    PATIENTS    LOGOUT

MEDICATION/SYMPTOMS

MAPPING - SIDE EFFECTS & SYMPTOMS PER MEDICATION — 205

EVERY MEDICATION HAS CERTAIN SIDE EFFECTS. USE THE DATA BELOW TO ADD OR REMOVE SYMPTOMS FOR THIS MEDICATION.

MEDICATION: [ VICODIN : HYDROCODONE ▼ ]

ASSIGNED SYMPTOMS — 206

CONSTIPATION : CONSTIPATION -
NAUSEA : UPSET STOMACH -

UNASSIGNED SYMPTOMS — 207

DEPRESSION : DEPRESSION -
DIAPHORESIS : PERSPERATION -
DYSPNEA : SHORTNESS OF BREATH -
ERYTHEMA : REDNESS -
FLATUS : PASSING GAS -
GASTRALGIA : STOMACH PAIN -
GOOD RECOVERY : GOOD -
HYPOHYDRATION : DEHYDRATION -
IMMOBILITY : IMMOBILITY -
INSOMNIA : INSOMNIA -
LEG PAIN : LEG PAIN -
LETHARGY : LACK OF ENERGY -
NOCICEPTION : PAIN -
PSYCHOLOGICAL : PSYCHOLOGICAL -
PYREXIA : FEVER -
TURGESCENCE : SWELLING -
TUSSIS : COUGH -
VASOMOTOR INSTABILITY : HOT FLASH -
VENTRAL SWELLING : SWOLLEN BELLY -
VOMITING : VOMITING -

CREATE A SYMPTOM — 208

MEDICAL TERM [          ]

COMMON NAME [          ]   [ ADD ]

*FIG. 2B* tapcloud
BETTER INSIGHTS, BETTER OUTCOMES.

HOME   PROCEDURE MAPPING   MEDICATION MAPPING   PATIENTS   LOGOUT

PROCEDURE/COMPLICATIONS    COMPLICATION/SYMPTOMS    SYMPTOM/KEYWORDS

MAPPING - SYMPTOMS PER COMPLICATION — 209

EVERY COMPLICATION HAS CERTAIN SYMPTOMS. USE THE DATA BELOW TO ADD OR REMOVE SYMPTOMS FOR THIS COMPLICATION.

COMPLICATION: [ INCISION SITE INFECTION ▲▼ ]

ASSIGNED SYMPTOMS — 210
- DIAPHORESIS : PERSPERATION -
- ERYTHEMA : REDNESS -
- PYREXIA : FEVER -
- TUMESCENCE : SWELLING -

UNASSIGNED SYMPTOMS — 211
- CONSTIPATION : CONSTIPATION -
- DEPRESSION : DEPRESSION -
- DYSPNEA : SHORTNESS OF BREATH -
- FLATUS : PASSING GAS -
- GASTRALGIA : STOMACH PAIN -
- GOOD RECOVERY : GOOD -
- HYPOHYDRATION : DEHYDRATION -
- IMMOBILITY : IMMOBILITY -
- INSOMNIA : INSOMNIA -
- LEG PAIN : LEG PAIN -
- LETHARGY : LACK OF ENERGY -
- NAUSEA : UPSET STOMACH -
- NOCICEPTION : PAIN -
- PSYCHOLOGICAL : PSYCHOLOGICAL -
- HASSLE : COUGH -
- VASOMOTOR INSTABILITY : HOT FLASH -
- VENTRAL SWELLING : SWOLLEN BELLY -
- VOMITING : VOMITING -

CREATE A SYMPTOM — 212

MEDICAL TERM [          ]

COMMON NAME [          ]   [ ADD ]

*FIG. 2C*

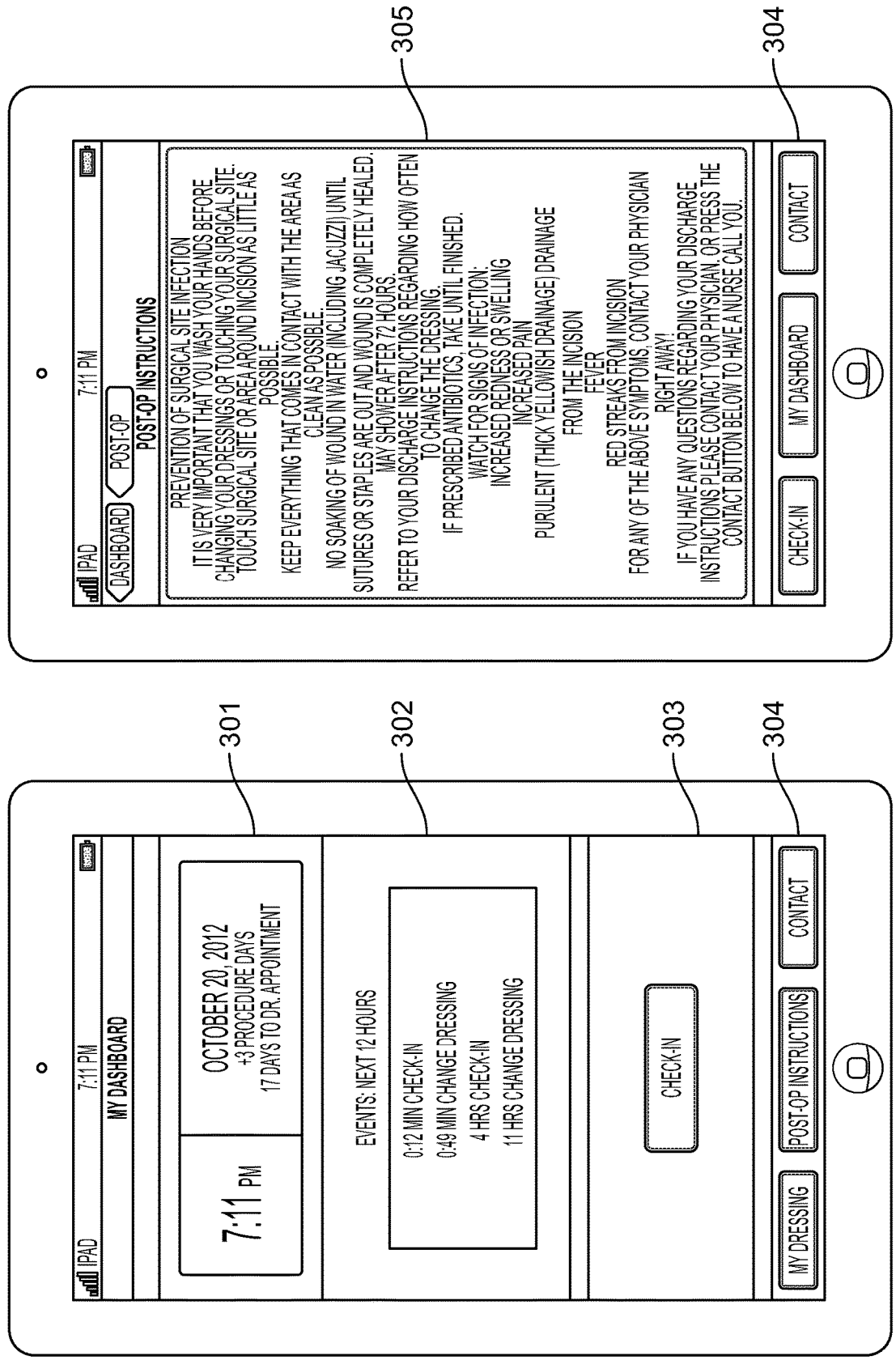

KEYWORD DUE TO KNOWN
PROGRESSION OF COMPLICATION
401

KEYWORD DOUBLE TAPPED TO
INDICATE HIGH INTENSITY
402

KEYWORD DUE TO COMPLICATION
403

CENTERED, DIFFERENTIATED KEYWORDS
DEPICTING PREVIOUS RESPONSES
404

KEYWORD FROM MEDICATION
SIDE-EFFECT PROFILE
405

LOWER BODY SWELLING    LIGHTHEADED
DIZZY    THROWING UP    GOOD MOBILITY
    WEAK MUSCLES    SHORT OF BREATH
        VOMITING    HEAVY SWEATING
DIFFICULTY BREATHING    COUGH    RED STOOL
    MIGRAINE    HEADACHE    NO ENERGY
        LEG SWELLING    TIGHT CHEST
    DIFFICULTY SLEEPING    COMFORTABLE    SLOW
        CONSTIPATED    BODY ODOR    CAN'T SLEEP
    CONFUSED    DECREASED APPETITE

+ ADD SYMPTOM    TO-CLOUD    SUBMIT

*FIG. 4*

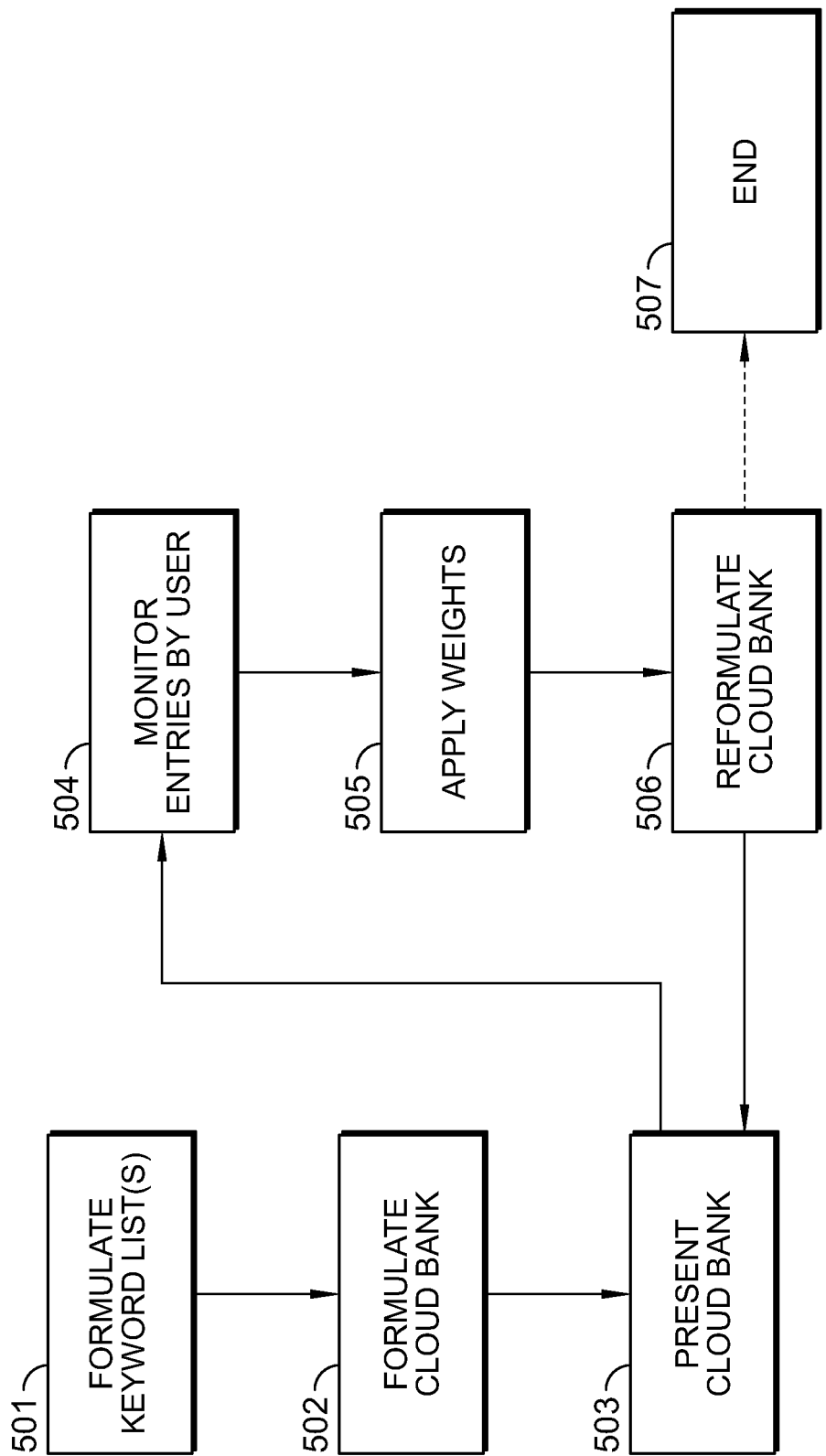

SYSTEM, METHOD AND APPARATUS FOR PROCESSING PATIENT INFORMATION AND FEEDBACK

RELATED APPLICATIONS

This application is a continuation of U.S. application Ser. No. 14/321,032 titled: "System, Method and Apparatus for Processing Patient Information and Feedback," filed Jul. 1, 2014, which claims priority to Provisional Patent Application No. 61/842,130 titled "System, Method and Apparatus for Processing Patient Information and Feedback," filed Jul. 2, 2013, which are both incorporated by reference in their entireties.

TECHNICAL FIELD

The present disclosure relates to computer processing devices, systems and networks configured to provide information to patients and to receive and process feedback provided by the patient in response to the information. The disclosure is also directed to structuring information provided to patients in order to maximize efficiencies in a feedback process.

BACKGROUND

It is well-known that when doctors have better information, they deliver better care to patients. Often times, having the capability to closely monitor patient conditions after treatment or after a procedure is as important as the treatment/procedure itself. Also, there is a need in the art to synergize the information being provided to a patient with the feedback provided to the care giver (e.g., doctor, nurse, etc.). Patients may not be clear regarding instructions, and may often be imprecise and/or inaccurate at recognizing and reporting symptoms. This in turn affects all areas of healthcare, from diagnosis to treatment, to compliance, to assessment of effectiveness.

One particular area of concern involves post-procedure monitoring, such as post-surgical discharge. In such circumstances, it is important for caregivers to be able to identify complications after discharge; in a recent study published in Journal of the American Medical Association (JAMA), 34,000 surgical patients were tracked to determine how complications affected caregiver costs and mortality rates. When no complications were present, the average cost of treatment per patient was estimated at $16,000 with a 0.6% mortality rate. However, when complications were present, the average cost rose to $56,000 average cost 12.3% mortality rate. As many of the complications are preventable, it is paramount that caregivers provide easily understandable information to patients which may be used to provide feedback to the caregiver(s) for processing. By utilizing intelligent information feedback systems, many complications may be caught early, resulting in significant cost savings and decreased mortality.

Information about a patient's well being, pain level, medication compliance, physical and emotional symptoms are important in every stage of healthcare from wellness to diagnosis to assessment of treatment effectiveness to care management, and eventually to end-of-life care. Despite the arrival of numerous internet-connected health care monitoring devices, the most important information about the patient can only be gathered from the patient themselves. Most, if not all, of these new technology solutions collect only objective biometric patient data.

The manner in which feedback is collected from patients is often inefficient, and, often times, ineffective. Typically, the feedback is solicited from static surveys that are often generic, but may be customized for particular maladies. Such approaches have been found to be less than effective for (a) presenting the correct keywords, (b) in an effective arrangement and (c) in an effective sequence for getting the most accurate and relevant information from a patient. Effectively capturing, organizing and sharing Patient Reported Information (PRI) is important for providing actionable and timely data analysis, combined with long-term, outcome-based studies. To be useful to both endeavors, PRI should be relevant, organized, accurate, contextual, and timely.

SUMMARY

Accordingly, under one exemplary embodiment, an apparatus is disclosed for processing patient data pursuant to a monitoring period, comprising a storage, a processor, operatively coupled to the storage, an input, operatively coupled to the processor, a communication, operatively coupled to the processor, and a display, operatively coupled to the processor. The processor may be configured to process patient feedback data received from the input and provide a keyword cloud to the display, and being selectable by the input. The keyword cloud may comprise a plurality of at least one of symptoms, complications and patient conditions, wherein the keyword cloud is structured by the processor for display in accordance with previous patient feedback data during at least part of the monitoring period.

In another exemplary embodiment, a processor-based method is disclosed for processing patient data pursuant to a monitoring period, the method comprising the steps of receiving patient feedback data via an input, processing patient feedback data via a processor, structuring a keyword cloud by the processor in accordance with previous patient feedback data during at least part of the monitoring period, and providing the structured keyword cloud to a display via the processor, the keyword cloud comprising a plurality of at least one of symptoms, complications and patient conditions.

In another exemplary embodiment, a processor based method is disclosed for processing and presenting patient data pursuant to a monitoring period, comprising the steps of retrieving and mapping a plurality of keywords from a structured database, each plurality of at least one of symptoms, complications and patient conditions, retrieving at least one previous patient data entry from a previously presented keyword, correlating, via a processor, the at least one previous data entry to at least one of the keywords, structuring, via a processor, a keyword cloud based on the mapping and correlating, and presenting, via a processor, the keyword cloud for interaction by a user.

BRIEF DESCRIPTION OF THE DRAWINGS

The present disclosure will become more fully understood from the detailed description given herein below and the accompanying drawings which are given by way of illustration only, and thus, do not limit the present disclosure, and wherein:

FIG. 2A illustrates a screenshot from processing and organizing keywords for symptoms under one exemplary embodiment;

FIG. 2B illustrates a screenshot from processing and mapping keywords for symptoms under another exemplary embodiment;

FIG. 2C illustrates a screenshot from processing and mapping keywords for symptoms per complication under another exemplary embodiment;

FIG. 3 A illustrates a screenshot of a client dashboard under one exemplary embodiment;

FIG. 3B illustrates a screenshot of instructions/reminders for a patient during a recover period under one exemplary embodiment;

FIG. 4 illustrates a cloud bank interface arrangement under one exemplary embodiment; and FIG. 5 illustrates an exemplary process for managing, mapping and formulating one or more cloud banks under an exemplary embodiment.

The figures and descriptions provided herein may have been simplified to illustrate aspects that are relevant for a clear understanding of the herein described devices, systems, and methods, while eliminating, for the purpose of clarity, other aspects that may be found in typical devices, systems, and methods. Those of ordinary skill may recognize that other elements and/or operations may be desirable and/or necessary to implement the devices, systems, and methods described herein. Because such elements and operations are known in the art, and because they do not facilitate a better understanding of the present disclosure, a discussion of such elements and operations may not be provided herein. However, the present disclosure is deemed to inherently include all such elements, variations, and modifications to the described aspects that would be known to those of ordinary skill in the art.

DETAILED DESCRIPTION

Figure 1:
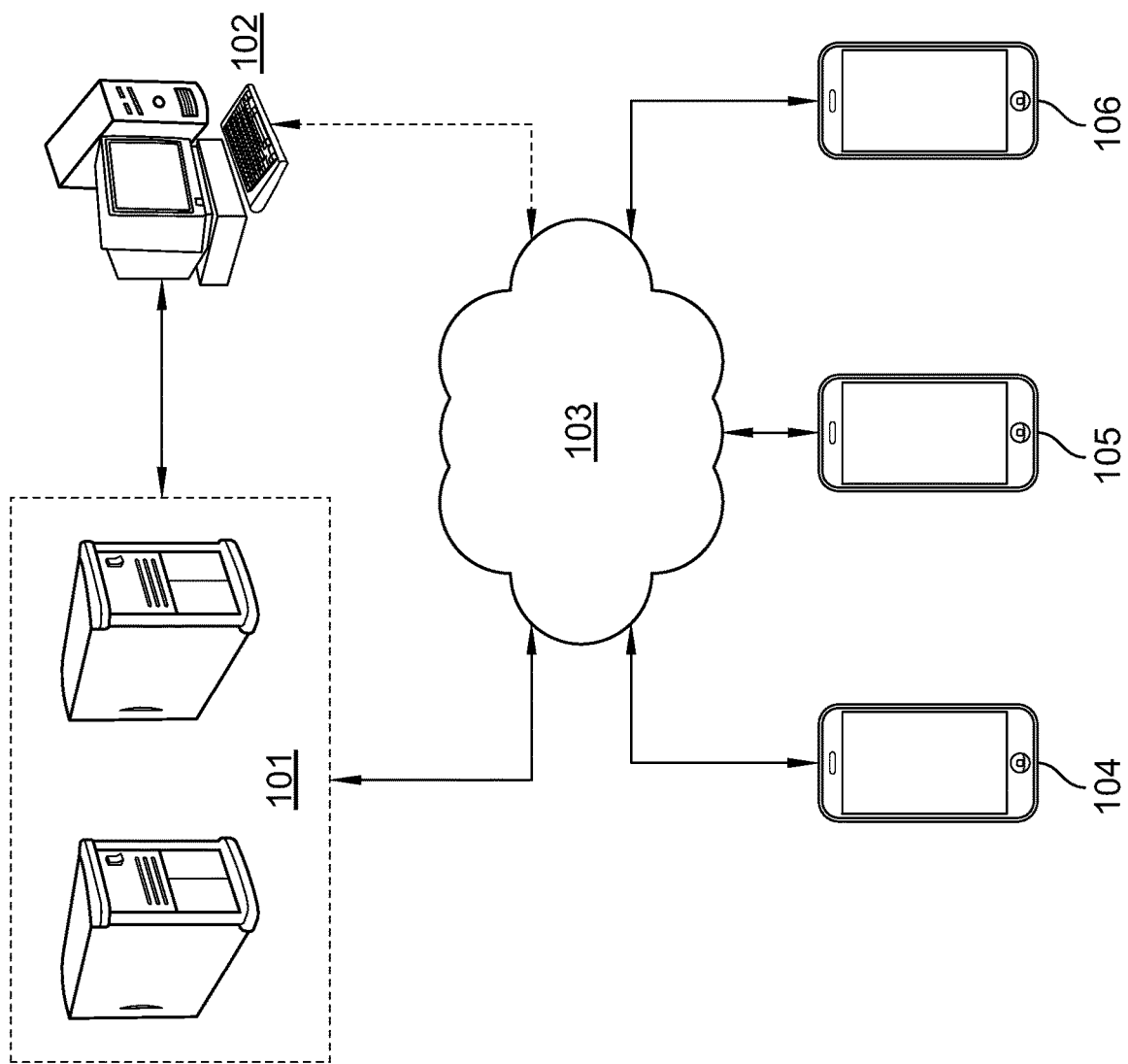
FIG. 1 illustrates a computer system for communicating and interacting with a plurality of user devices under one exemplary embodiment.

FIG. 1 provides one exemplary embodiment of a system configured to provide and receive information and/or feedback from patients. In a preferred embodiment, servers 101 are configured to store and process patient information that may include feedback. Servers 101 may comprise one or a plurality of servers that may be distributed across multiple locations. For example, one server may be located on a caregivers premise and may be communicatively coupled to a second server located at a service provider's location. Server configuration, information and data may be initialized and updated by one or more workstations 102 that may also be configured to control transfer of data between multiple servers. Workstations 102 may be configured as personal computers, laptops, tablets, and the like. Servers 101 are configured to communicate to a network 103 which may be a TCP/IP network such as the Internet. Alternately, network 103 may also include wireless and/or telecommunications networks known in the art. Network 103 may facilitate communication between servers 101, and also provide means of communication to one or more remote processing devices 104-106. Devices 104-106 may be smart phones, tablets, laptops, or any other suitable portable processing device.

The system of FIG. 1 is configured to communicate and monitor patient progress through at least a portion of a recovery cycle beginning pre-discharge, and intelligently probes (via servers 101 and devices 104-106) for side-effects of medication, and other warning signs that may not be apparent to patient. The system may be further configured to provide a visual record of the healing of external wounds and prompt patients to follow doctor's orders and evidence based guidelines. Additional integration may be done by linking in other external monitoring devices into the system. Servers 101 may be thought of as a "back-end" for the system of FIG. 1 and comprises an artificial intelligence (AI) that allows patient interaction to be customized for their condition or procedure, and includes data pertaining to medications, phase of recovery, previous responses and specific doctor's instructions. An intuitive cloud-based interface is provided to simplify the process through which patients report on key aspects of their condition for review by clinical staff. Additionally, the interface provides customized evidence based guide for in-home procedures like changing wound dressing to improve patient compliance.

Under a preferred embodiment, each of devices 104-106 are equipped with specialized software that enables the device to execute applications, receive input from patients, and communicate to/from servers 101. In one example, each device is provided to a patient prior to discharge from a hospital. It may be configured for them specifically based on the type of surgery they had, type of anesthesia used, pain medications to be taken post-discharge, antibiotics used post-discharge, recovery instructions, etc. The configuration of devices 104-105 may be provided by server(s) 101 which "push" specific operational configurations to the device which may be initialized and/or modified via workstation 102. The device configuration may also include both general post-operative guidelines as well as any specific instructions from the medical team for the specific patient. The software for each of devices 104-105 are preferably configured to interact with the patient several times per day to gather information from the patient on how they are feeling, and watch for indications of complications. Data gathered by the device will be available for the patient's doctor and/or hospital staff in real-time through an online web portal, and/or a daily report may be assembled and delivered via fax or secure email as well.

Figure 3C:
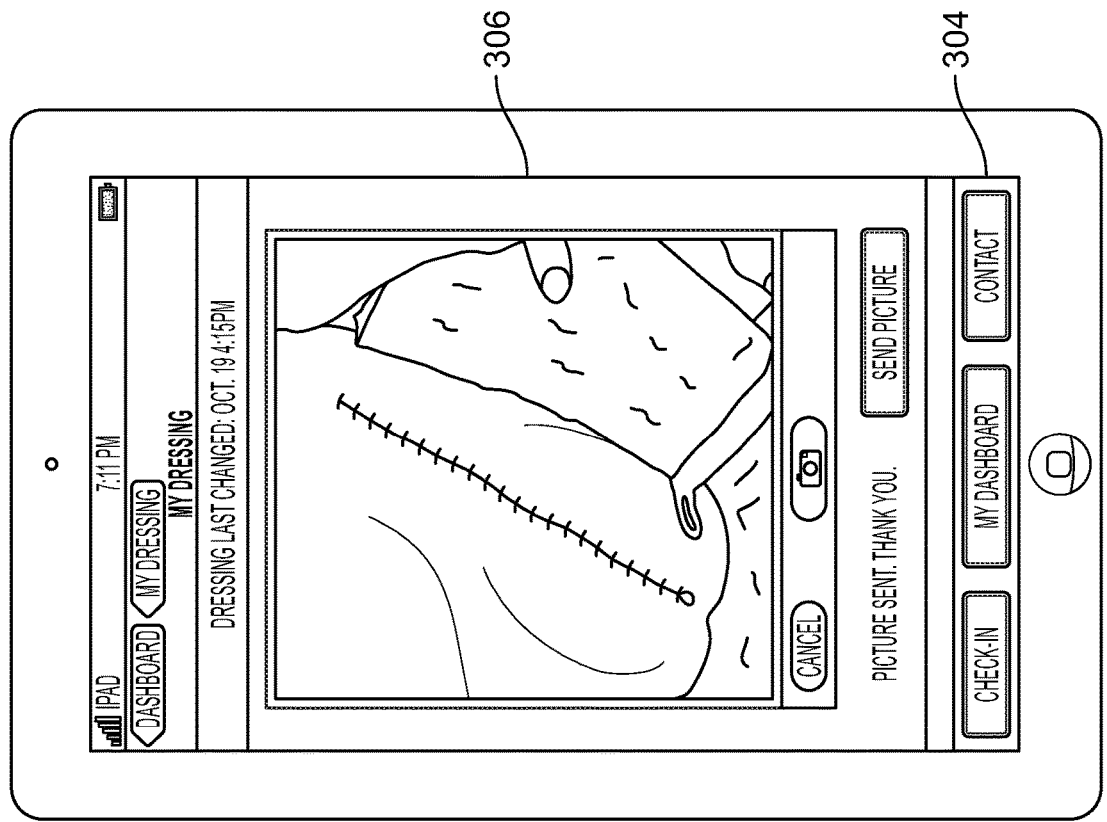
FIG. 3C illustrates a screenshot of a patient photo interface under one exemplary embodiment.

The software is designed to focus on engaging the patient during their recovery from their surgery until the post-operative follow-up visit with their doctor, at which time the device will be collected, digitally and physically cleaned and readied for its next use. User interaction with the software may include a training mode and a dashboard (FIG. 3 A) with detailed listing and/or instructions of things the patient is supposed to do (FIG. 3B) during their recovery period, including automatic reminders for things like changing dressing, taking antibiotics, and pain medication. Additionally, an evidence-based checklist for procedures like incision care may be provided, along with visual indicia feedback (FIG. 3C) to allow the patient to take a photo of their physical state (e.g., incision during a dressing change). Furthermore the device may be configured so that a unique "cloud" of symptoms (FIG. 3D) may be presented to the patient with each interaction that allow a patient to easily indicate issues they are having. The cloud may take into account all the inputs provided by the hospital staff as well as prior responses by the patient.

The back-end system (101) should be configured to organize the cloud in such a way as to probe for specific symptoms and recognize both positive and negative responses as providing insights that can be tracked and used in formulating future versions of the patient's cloud. The patient may be able to create their own entries separate from the ones suggested by the cloud and be able to enter a question or concern that they want to bring to the attention of the clinical staff, and the software should allow an answer from the clinical staff to be displayed to the patient. Under one embodiment, the software may not retain the patient's name or any other identifying information except for the patient ID from the hospital and potentially patient ID's from their caregiver or other clinicians involved in their care. The software is configurable to allow for modification of the preset schedule for things like medication or dressing changes while retaining the intent of the clinical guidance. For example if antibiotics are supposed to be taken every six hours, the patient should have the ability to set up a time that is convenient for them, while the device will continue to remind them every six hours. The software allows patients to easily record that they have taken meds, performed a dressing change, etc. and should allow the patient to view a record of when they have taken medication or performed a dressing change so they can see their performance over time. This configuration is particularly advantageous for allowing patients to plan for their next interaction.

A Patient Coordinator (PC) may also interact with the device software via workstation 102 over network 103. As mentioned above, the workstation 102 may be used by the PC to configure the patient information into the system and create the unique inputs that will define the patient's cloud and clinical guidance. Under one embodiment, this configuration may be a combination of drop-down selections and free-form entry of information. The PC may register the app to the patient capturing the serial number of the device being used for inventory control and monitoring purposes. Once activated, the device should first go into Training mode, described in greater detail below. The PC may have options for configuring or modifying data based on how the training goes. For example, an "easy" mode may be provided for people with no tablet experience, or an "advanced" mode may be applied for people who can manage double tap, swipe, or other device functions. At the completion of the orientation, the device can be activated for actual use. The PC may also identify other contact info for caregivers, which may be added to the patient record for alerts.

In one embodiment a device may enter a "training mode" shortly after initial activation. Operation/execution of the training mode should preferably be only from the device, as hospitals frequently prohibit cell signals. During a training mode, an audio/visual presentation is run to provide information relevant to the patient, and provide contact information for the patient's caregiver and/or others that may be connected with the patient's caregiver. A software tutorial (e.g., interactive tutorial) may also be presented, where the patient is informed on the device and software operation, along with other information directed to charging the device, connecting to the network, troubleshooting, how to check in periodically, how/where to return the device when the recovery is complete, etc. Additional information regarding reminders, using the schedule, following checklist(s), taking photographs, etc. may also be provided.

During a non-clinical monitoring mode, a portal may be provided (101) to allow back-end visualization of all devices in use, together with locations of devices via GPS/location services. Under a preferred embodiment, clinical content is separated from non-clinical monitoring. A dashboard may be provided to show status of each device and the last interaction time and type, where dashboard information may be used to provide reminders (automated or manual) based on the received data. Reminders/responses may be generated under a variety of circumstances, including:

A patient has not used device for a predetermined period of time;
A patient has missed a number of activities in a checklist;
A battery state is below X %;
A device has not checked in for a predetermined period of time;
If patient has not responded to or opened an automated message;
A patient has generated an error message in their usage of device;
A device is more than a predetermined distance from an authorized usage area;
A device loses network connection for a predetermined period of time;
Reminder to schedule follow-up appointment (w/ link to contact info);
New messages received (w/ link to message page); and
If device shows same location as hospital, confirm visit has taken place.

The reminders/responses may be provided in the form of text messages, MMS messages, email, push notifications to the device, scripts, and the like. In certain circumstances, reminders/responses may be in the form of telephone calls ("escalation"), particularly in cases where the device and/or user is nonresponsive.

For a clinical monitoring mode, clinical information and data is provided for a caregiver for analysis. Under a preferred embodiment, an online web portal receives and communicates real-time updates on patient conditions. Daily summaries via secure email or other messaging may also be provided. For an inventory mode, the system's dashboard enables visualization of all devices that are in use, in inventory, scheduled, scheduled for return, in transit, etc. Device can be registered into the system manually by serial number or by QR code. Predictive analytics may be added to inventory mode to determine when devices will be available.

One of the important aspects of the present system is the manner in which diagnostic feedback (see FIG. 3D) is communicated between a caregiver and a patient. It is known in the art that the types of words and/or phrases, and the manner in which they are presented, have an effect on user responses, particularly in the cases of "word clouds" or "tag clouds." While tag clouds are well known in the context of digital data and digital document processing, little work has been done regarding the use and configuration of word clouds in obtaining patient feedback for identifying potential conditions and/or complications. Accordingly, the system of FIG. 1 should be configured to efficiently present feedback options in order to obtain more accurate analysis of symptoms.

The present system is preferably configured so that symptoms are linked to keywords that may be used in feedback analysis. In the example of FIG. 2A, symptoms (pyrexia) are provided assigned keywords (e.g., "can't get out of bed," "chills," etc.) which may be linked to the symptom. When at least some of these keywords are presented to a patient (FIG. 3D), and selected by a patient, this feedback from the keywords becomes indicative of one or more symptoms that may be present. Unassigned keywords (e.g., "anxious," "better," etc.) may be remotely linked to the symptom, indicating that there may be a non-definitive correlation to the symptom. Under a preferred embodiment, unassigned keywords are often linked to multiple symptoms. In order to determine specific links and correlations, assigned and unassigned keywords are preferably assigned individual weights, where keywords known to have a high correlation to a symptom are given higher weight values (more directly linked), while keywords known to have a low correlation to a symptom are given lower weight values (more remotely linked). When processing keyword feedback from a patient, the weight values may be used to determine symptoms that may be present. Thus for example, if a few highly-correlated keywords are selected by a patient, the system will be able to process the feedback to determine the symptom(s) present. Similarly, if many lower-correlated keywords are selected by a patient, the overall weight value may nevertheless determine that a sufficient correlation exists to a particular symptom.

Figure 2D:
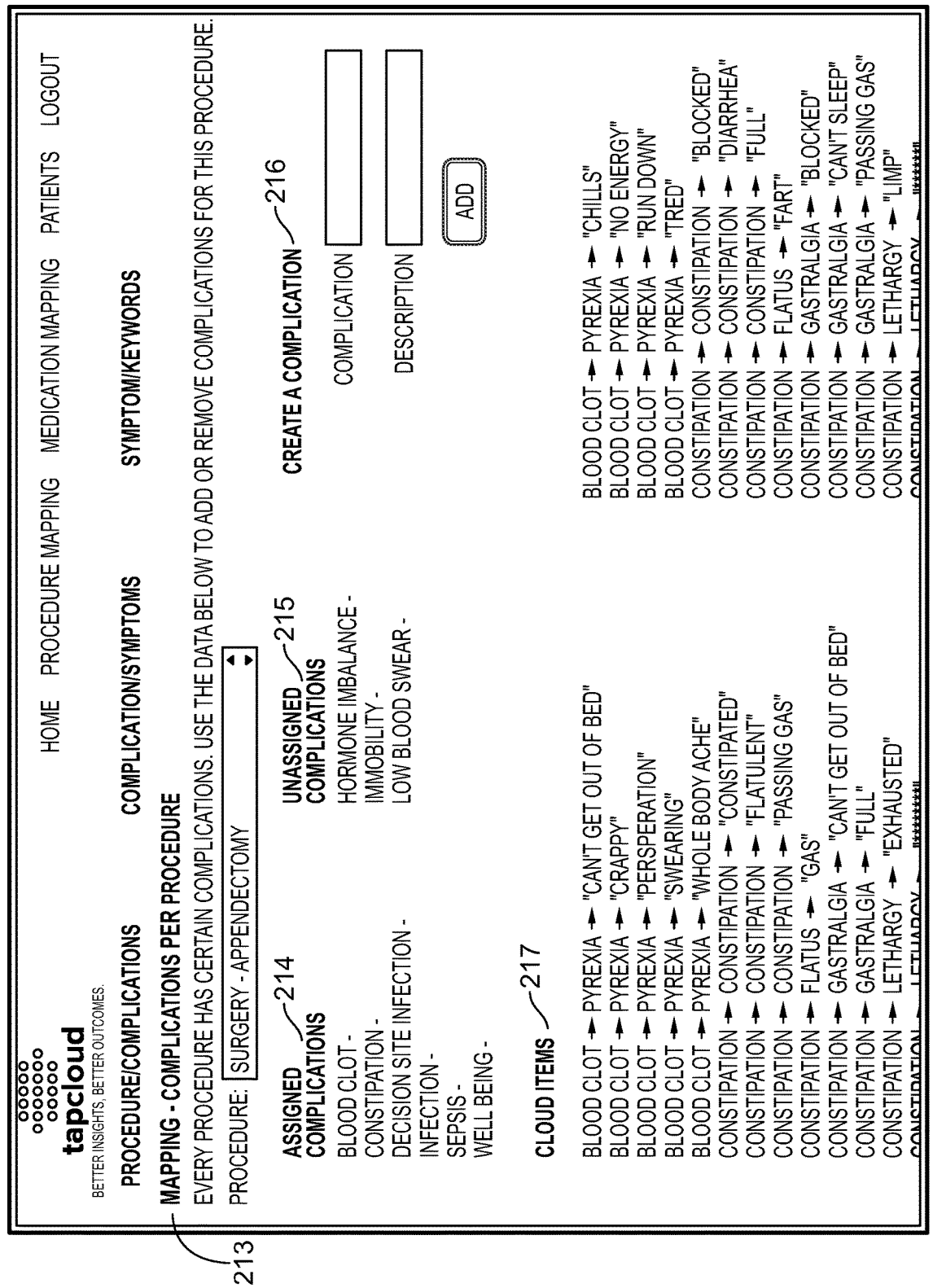
FIG. 2D illustrates a screenshot from processing and mapping keywords for complications per procedure and formulating a cloud bank under yet another exemplary embodiment.

It should be understood by those skilled in the art that the weighted correlation threshold for a symptom may be varied, depending on the symptom. Additionally, multiple keywords may be clustered or grouped to form multiple thresholds for a symptom. Furthermore, multiple symptoms may be linked as well. In such a case, the determination of one symptom may trigger another presentation of keywords to a patient correlated to one or more other symptoms. Such a configuration may be advantageous in cases where a plurality of conditions and/or complications is linked to one or more symptoms. As can be seen in the example of FIG. 2B, symptoms and keywords may be correlated to medications as well (Vicodin). Similar to the example in FIG. 2A, the feedback to communicated keywords may indicate conditions and/or complications that are correlated to a particular type of medication. The example of FIG. 2C illustrates another embodiment where symptoms and keywords are correlated to a specific complication. Again, a weighted correlation of keywords to symptoms may be advantageous in situations where a specific complication needs to be monitored. The example of FIG. 2D illustrates another embodiment where symptoms and keywords are correlated to a complication associated with a specific procedure. Once more, a weighted correlation of keywords to symptoms may be advantageous in situations where a specific procedure needs to be monitored.

As can be appreciated by those skilled in the art, the aforementioned configurations can provide a powerful tool in establishing correlations between keywords selected by a patient and symptoms that are likely to be experienced. As the keywords are modifiable and capable of being communicated in "user friendly" terms (i.e., layperson), the patient may be capable of communicating more effectively to the caregiver.

Under one embodiment, semantic annotation techniques are used to arrange and configure keywords with symptoms. Medical concepts often have alternate names (synonyms), one of which may be easier for the patient to understand than others. A first linking may be provided by linking a term with synonyms and, more specifically, providing its more comprehensible synonym. For example, "pyrexia" is easier to understand if "perspiration," "sweating" and/or "whole body ache" is also provided in parallel. Similarly the medical abbreviation "OD" in medication intake contexts is easier to understand if "once daily" is also provided. These semantic annotations are advantageous in overcoming vocabulary differences and to provide user-friendly synonyms. Under one embodiment, the keyword lexicography of the present system may be based off of a Consumer Health Vocabulary (CHV) tied to a semantic annotation platform residing in 101, which may be part of a knowledge information management (KIM) platform. Semantic annotations may be performed in the KIM by creating and/or generating semantic annotations for each target vocabulary word or term (keyword) using a predefined ontology. The annotations stored in the system maintain semantic descriptions of the vocabulary in the form of instances, relations and attributes. The ontology may be extended to include "preferred" words or terms and aliases, compared to other, less relevant, words to represent classes within the vocabulary. Thus, for each target vocabulary word and subsets thereof, classes of preferred terms, synonyms and aliases may be linked. As an example, a symptom defined as "pyrexia" would be identified as an instance of "perspiration," "chills" and "whole body ache" in the metadata (tags), where any further aliases or synonyms may be further linked as related data.

The classifications for the data structures may be managed by one or more classification algorithms. Certain classification algorithms may learn by example using data that has been organized into classes manually or through some other automated process. Through the training process, the classification algorithm may determine which properties (or features) indicate that an item belongs to a given class of objects. When trained, classification algorithms can classify previously unlabeled data. In another embodiment, clustering algorithms may also be used. Both of these types of algorithms may be used to assign labels to objects using the features of those objects to determine the appropriate assignments. Classification differs somewhat from clustering in that classification may use a predefined set of labels and learns how best to fit objects into this scheme. This approach is sometimes referred to as "supervised learning," where the labels assigned by the classification algorithm are based on external input such as a human-defined set of categories. Clustering is a type of unsupervised learning that doesn't necessarily use a predefined set of labels. Clustering forms groups of objects based on common characteristics.

Classification algorithms may also learn by example, using training data that has been organized into classes manually or through some automated process. By observing the relationship between features and classes, the algorithm may learn which features are important in determining the proper label and which keywords provide little or misleading information about the appropriate label for the symptom in question. The result of the training process is a model that may be used later to classify previously unlabeled objects. The classifier processes the features of the objects to classify and uses its model to determine the best label for each object. Depending upon the classification algorithm used, the classifier may emit a single label or it may emit multiple labels, each accompanied by a score or probability that ranks the label against other possible labels for the object in question. There are many different types of classification algorithms. There are binary algorithms that produce two discrete outcomes, such as a yes/no answer. Other algorithms support multiple outcomes, producing a result from a discrete set of categories or a continuous value, such as a floating-point score or probability.

Binary classifiers produce an indication whether the object being evaluated is a member of a class. Bayes classification algorithms are capable of developing a statistical model in order to determine whether an object is a member of a class. Support vector machines (SVM) may also be considered a binary classification algorithm, which attempts to find a line or n-dimensional plane known as a hyperplane that will divide the feature space between examples within a class and outside of a class. Binary classifiers may be combined in order to perform multiclass classification. Multiple binary classifiers may each be assigned a class, and input is evaluated against each class to determine which it falls into. Depending upon the algorithm, the output will be a single class that the input is most likely to fall into or a number of classes that the input is a member of, each weighted in some way to describe the relative likelihood that an object is a member of a given class. A Mahout Bayes classifier is another example of a technique for training many binary classifiers in order to assign categories from a multiclass classification scheme.

Multiple binary classifiers may be organized in tree-like structures. In such a case, an object that falls into class A, which has child classes B and C, will be evaluated against the classifiers trained for each class B and C. If it matches B, it'd be evaluated by B's children, E and F. In cases where a document fails to be assigned to either E or F, it may be considered to be in B; otherwise the document is assigned to the lowest level leaf category it matches. This approach is useful where the classes are naturally hierarchical in nature such as in a topic taxonomy. Variants of this hierarchical approach have been used to great effect in approaches such as hierarchical binary decision trees and random forests.

Using a statistical classification algorithm (e.g., Bayes), the probability of a set of keywords belonging to a given category may be determined. Typically, Bayes' Theorem is used to invert the conditional probability in order to determine the probability of a category, given a set of keywords. Other statistical classification algorithm may be used to model the probability of a category given a set of words, without first having to determine the inverse relationship. The naive Bayes classification algorithm is a probabilistic algorithm that builds a model based on relationships between features and categories in order to perform keyword categorization. Another statistical algorithm, referred to as a "maximum entropy algorithm" (Open NLP), may be used to construct a model using a regression algorithm to determine how category features relate to sub-categories. Weights for each feature are determined and processed to produce an output that's most similar to the outcomes observed in the training data. Thus, under one embodiment, as symptoms/complications/keywords are categorized, features are generated upon which those categorization decisions are based. This is approach is sometimes referred to as "piggybacking," where one classifier is trained using the output of another classifier.

With regard to the regression algorithm, a multinomial logistic regression model is one exemplary regression model that is suitable. Generally speaking, regression models are concerned with determining the relationship between a dependent variable and a number of independent variables. Each regression model is a function with a weight for each feature. When these weights are combined with values for each feature and the weighted features are then combined, the result represents the model's prediction or outcome. The regression algorithm is tasked with determining the appropriate weights for each feature based upon the outcomes observed in the training data.

For keyword categorization, the output of the regression model (the dependent variable) corresponds to the output of a classifier (e.g., a category label produced by a categorizer). The input into the regression model (independent variables), may be though of as features, or aspects of the keywords, in the classification context. Thus, keywords may be treated as independent variables. Trained features may be thought of as "predicates" (keywords) within one or more contexts (com-plication, medication). Each predicate may be used in the model as an independent variable to predict the value of the dependent variable where the contexts map predicates to outcomes. These mappings may be determined and improved during a training phase, where observed results may help determine the accuracy of the model; a series of iterations may also be performed in order to find the best weight for each predicate in order to produce a desired outcome.

Figure 3D:
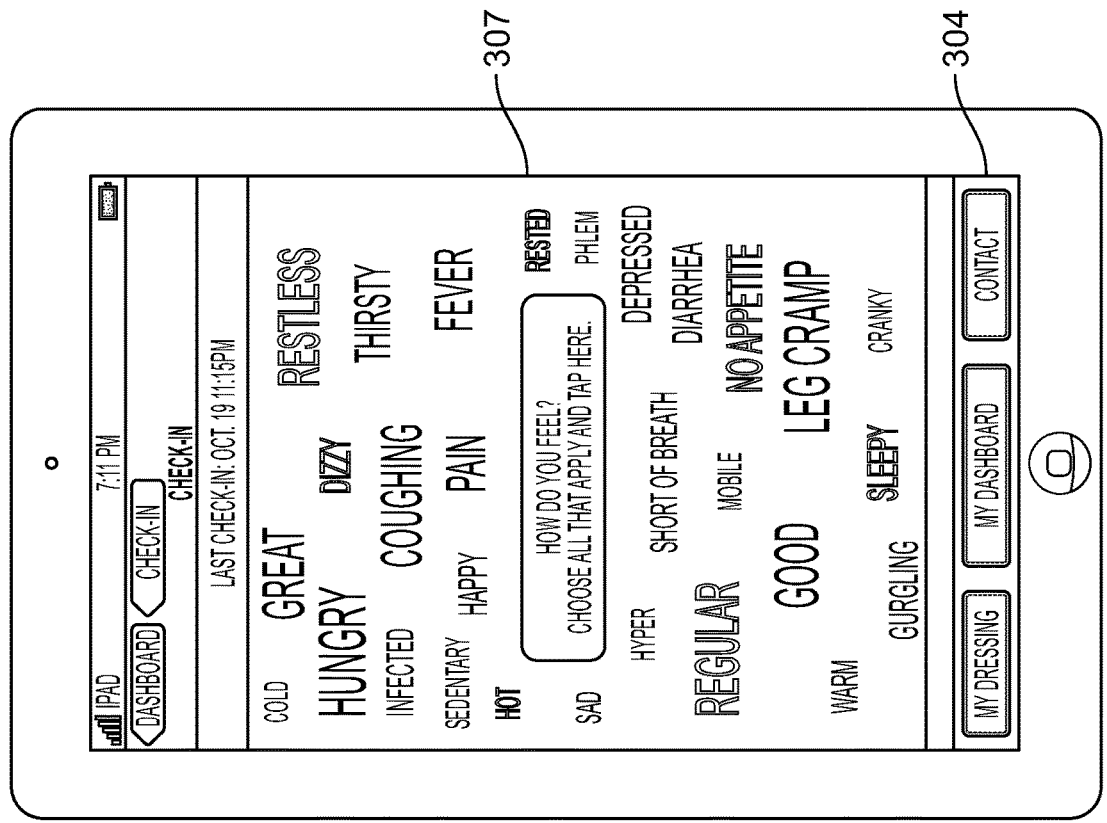
FIG. 3D illustrates a screenshot of a cloud bank display under one exemplary embodiment.

Turning to FIG. 4, and with reference to the embodiment of FIG. 3D, an exemplary keyword cloud structure is provided. As can be seen in the figure, cloud keywords may be provided according to known progression(s) of complications 401, together with one or more keywords related to complication(s) 403 and medication side-effect profiles 405. As keywords are interacted with (tapped) by patients, their display may be enlarged, highlighted, colored, etc. 402 to indicate the selection has been made. Similarly, previous selection are preferably clustered and/or centered 404 to allow for differentiation of keywords from previous responses. Under one embodiment, the clustered keywords 404 may also be enlarged, highlighted, colored, etc. for further differentiation.

As disclosed previously, an exemplary check-in process may begin with a question seeking user entry data relative to a previous point in time or previous reporting period (e.g., "Flow do you feel today, compared to yesterday?"). The question is formulated as such due to the fact that the system and feedback database provides a trajectory of how a patient feels, rather than an arbitrary score. Accordingly, several days of entry data in a relative day-to-day context (or trend) provides more insight than entering a fixed data point (e.g., going from a 7 to a 5 on a rating's scale). This type of data entry query also does not require reflection or lead to over-thinking on the part of a patient. Such a configuration has been found to advantageous in allowing patient to reflexively answer queries relative to a previous data point (e.g., the day before).

The keyword cloud configurations disclosed herein have been advantageously found to aid in the retrieval process of memories without generating a bias. Ordered lists and standard questionnaires generate both bias and inaccurate PRI. A typical patient survey provides a list of symptoms with a 1-10 scale from good to terrible. In addition to memory encoding issues, a survey of this type also suffers from a lack of context. Stated another way, is a particular symptom rated high because it is bothering the patient right now, because it occurs frequently, or because it has a strong quality of life impact? Existing standards for patient engagement and symptom inventory surveys do not provide actionable insights because they can't provide context.

The presently disclosed system reduces bias by stimulating retrieval of information in a way that causes the user's brain to actively access the hippocampus and simultaneously the left and right hemispheres. By constantly varying both the word choices and the visual appearance of the cloud, we stimulate the spatial/creative and language/memory regions of the brain, which creates a much more engaging and attentive experience for the patient. Furthermore, by interacting with the patient in a brief daily check-in, the present disclosure eliminates the need for a patient to remember how they felt last week, and instead focuses on understanding how a patient feels in a present moment. This combination creates the most accurate record of PRI available.

Identifying and recording specific medically relevant symptoms customized for each patient is important. The ability to probe for specific symptoms without creating a bias is important to obtaining accurate PRI. Capturing subjective symptom information requires an understanding of both memory and attention. Memory is the ability to recognize information not in conscious awareness. Memory goes through 3 processes: Encoding, Storage, and Retrieval. To ensure the present disclosure's Patient Reported Information (PRI) is as accurate as possible, and not influenced by the survey methodology, the disclosure minimizes the first two stages so as not to influence future responses, and maximizes the last stage—Retrieval—to increase the accuracy of the information.

The human brain can encode in two different ways—automatic and effortful. For the purposes of gathering PRI, the present disclosure is concerned with the type of encoding that occurs automatically. Typical methods of gathering patient's medical information include surveys which cause automatic encoding. Automatic encoding occurs with little or no effort and an enormous amount of information about space, time, and frequency is stored. This type of encoding occurs without our awareness and without interfering with our thinking about other things.

With repeated use of existing patient surveys, it is typical for a user/patient to subconsciously (or automatically) encode the location of a particular question and how they have previously answered said questions in the past. This greatly affects the accuracy of the survey process, essentially making the survey a mechanical, non-thought provoking procedure where patients are answering the questions similar to their previous responses and generating a biased base of information. They are in a sense trying to remember both how they felt in the past, and simultaneously how they answered the survey previously.

To combat the natural tendency of the human brain to automatically encode any part of our PRI collection system, the present disclosure presents medically relevant keywords in a word cloud designed to minimize false memories or mixing symptoms felt with previous responses to the survey. The present disclosure further reduces reliance on memory by asking the patient to only record the symptoms they experienced that day.

To understand how the present disclosure creates a personalized, relevant, patient interaction that stimulates and engages a user while monitoring for adverse health trends, a backend clinical mapping system, used in conjunction with the configuration of FIG. 1 under one embodiment, is used to ensure each response is medically relevant and allows the system to structure PRI data for both real-time care management and research and analysis. The system is particularly advantageous for patients that have, for example, (i) been diagnosed with one or more chronic conditions, or have recently undergone an acute event such as a trauma or surgery, (ii) participating in a clinical drug trial or research project, (iii) may be pregnant or be preparing for a surgery, or have recently started a new medication, and/or (iv) setting fitness, weight loss, or stress reduction goals. Any scenario involving changes to a patient's physical, psychological or emotional health that will benefit from understanding the day to day experience of a patient's well being or pain levels, or that involve monitoring for specific symptoms, will be improved by the use of the presently disclosed system.

The system may initially be configured based on a patient's existing medical profile and the medications and supplements they are taking. This information may be gathered from a medical provider, insurance company, care management company, or from the patient themselves. Based on a diagnosis, augmented by any additional diagnoses and specific medications, the present system creates a map of known complications associated with that diagnosis/condition/procedure (see, e.g., FIGS. 2A-D), which may then broken down into symptoms that would be of concern to a medical staff. Each of these symptoms is then translated into everyday language that a patient would use in describing such symptoms. For example, Abdominal Pain might be displayed as "Stomach Ache."

Repetition of meaning, or synonyms, is used to ensure that all patient reading levels are accommodated. The cloud's intelligence engine "learns" the words that a user/patient chooses and will increase the probability of those words being relevant in future iterations of their cloud (e.g. tired vs lethargic). Keywords can also be translated to multiple languages using the same clinical mapping structure. This allows for a multi-lingual patient experience.

A side-effect profile (see, FIG. 2B) of each medication being taken by a patient is mapped using a similar process. All of the side effects are rendered into everyday language keywords that a patient would use to describe such symptoms. Medication side-effect keywords are also adjusted for literacy levels and can be translated into any language. From a patient perspective, medication and condition keywords are indistinguishable so as not to create any bias, positive or negative in PRI. In one embodiment, a regimen of questions may be tailored for a new treatment or medication may be structured in the context of, "Is it helping?" The answer to that question is found in observing the elimination of undesirable symptoms, combined with the lack of unwanted side effects.

The mapping of both affliction keywords and medication side-effect keywords is provided in the exemplary embodiment of FIG. 5. The process for keyword cloud formation may be generally described in terms of 3 broad concepts: (1) generation, (2) presentation and (3) interactivity. The data base selection should preferably be concise, presenting, for example, 20-30 words on average. The keywords should be relevant to the patient's condition(s), and strategic for identifying clinically relevant data, including but not limited to: any complications directly or indirectly related to their underlying condition(s), psychological constructs, physical manifestations, and medication effects and side effects.

An exemplary keyword cloud may be constructed in real-time using multi-step algorithms to collect, analyze, and assign weights to any and all appropriate potential symptoms (keywords). A list of possible keywords 501 is used to populate a temporary "cloud hash" in memory. This cloud hash is the middle ground between the raw keywords and the finished cloud object. Keyword candidates may be added to the hash and variables associated with each keyword are increased or decreased by algorithms to identify the most desirable words.

Referring to FIG. 5, key word lists may be formulated 501 from existing lists, as well as all keywords in a user's current cloud bank are added to the hash. The user's cloud bank may comprise all cloud words previously selected and/or entered by the user. Clouds may include any words selected by the user in the most recent cloud. This includes both words selected ("tapped") 506 by a user and those entered directly into the cloud by the user, caregiver, doctor, nurse or care manager ("custom words"). These words are identified in the cloud bank and weighted 505 accordingly.

Next, all words selected and/or entered from a predetermined number of previous days (e.g., 7 days) are considered for inclusion in the final cloud during formulation 502 and may be taken from reformulated cloud bank processing 506. The predetermined number of days may also be made dependent on a variable based upon how many words this user typically selects in a cloud and how many clouds the user typically submits in a day. Custom words may be uniquely identified in the hash so-as to enable enhanced weighting 505.

A diagnostic tree database may be traversed in 502 to select one or more "most appropriate" keyword representing each possible physical symptom, psychological indicator, and medication related side effect. These words are added to the cloud hash.

Custom algorithms are applied to the cloud hash to assign weights to each word 505. Some keywords, such as those that have appeared in the most recent cloud, may be marked as "must have". These algorithms consider multiple variables, including but not limited to: recency score, frequency quantity, frequency score, tap sum, tap score, total score, and must haves. All "must haves" and the top scoring keywords may be selected from the cloud hash and prepared for presentation in the cloud 503.

In the present embodiment, each cloud is uniquely created for each interaction based on the patient's recent responses, correlation to known disease progression, medication side effects, and linkage to patient activities. Regarding presentation, when keywords are displayed to the patient in cloud form (FIG. 4), the cloud will display the keywords from the patient's most recent check-in, near the center of the cloud, preferably in a font that differentiates them from the rest of the keywords. This is done as a subtle reminder to the patient of what they reported most recently and it helps identify both ongoing issues and serves to highlight when a particular symptom goes away. Otherwise, specific cloud presentation may be randomized to create a different visual appearance for each interaction. Once a predetermined monitoring period has ended, and/or by specific instruction to do so, the process of FIG. 5 may be terminated in 507.

Regarding interactivity, a patient interacts with the cloud 504 by touching one or more words that they feel apply to their current condition and/or state of mind. Touching a word may provide tactile, audible and visual feedback indicating the word has been selected. Touching the same word again provides a higher level of feedback. Touching the same word a third time returns the word to a "deselected" state. If the user is experiencing a symptom or emotion that is not present in the displayed cloud, they can click on an icon to enter any word that describes how they are feeling that day. This allows the patient to track any symptom large or small, because it is frequently the small symptoms that left untreated, end up becoming big problems. One day of diarrhea is unpleasant. Two days will put an at-risk patient in the hospital. Three days is life-threatening for anyone. Once the user is done selecting or entering keywords, they tap a button on the screen to submit their selections.

Standard surveys, questionnaires, and symptoms inventories use the same form every time which leads to a patient giving less and less cognitive thought to the information retrieval process because subconscious encoding creates the feeling that the patient has already completed the survey. Patients resist filling out the same form repeatedly, and begin to think of the task as a chore to be dealt with, not an opportunity to capture important insights. Because patient surveys and symptom inventories are done usually a few times per year, the accuracy of the patient information is heavily biased towards how they are feeling that day which may completely miss something serious that occurred last week.

The present disclosure captures simple, yet relevant information about how a patient is feeling day-to-day, while watching for symptoms that are clinically important for their personal health situation taking into account current diagnoses, all medications, and all previous responses. And by doing this with a brief one-minute check in each day, a real-time stream of data that can be used by doctors and nurses to actively manage at-risk patients, identify onset of a new complication, assess medication effectiveness, and help manage quality of life issues. By presenting different clouds each time a patient interacts, we reduce the tendency to automatically encode any part of the symptom cloud. By maximizing the authentic nature of the recall stage, retrieval cues or items that provide reminders of information may be minimized. By allowing a patient to use random discovery methods, patients intuitively spot the symptoms that are presently being experienced without an inherited bias. By repeatedly displaying a variety of possible symptoms, patients are subconsciously educated on specific things to watch for which increases their engagement and self-awareness.

In summary, the present disclosure describes systems and methods for capturing information about a patient's daily activities in a variety of ways. A customized care plan may be displayed for each patient that can include medications, activities, recording vital signs, and reminders. The care plan can also include detailed instructions for an at-home procedure, for example changing a bandage or caring for a wound. This care plan is initially derived from the patient's primary condition and is further customized both by their care team and the patient themselves.

Each activity in the care plan may be set up with alerts for the patient throughout the day (for example a reminder to take a particular medication at 3 PM every day), or the patient can choose to record an overview of their activities at the end of the day. For each medication or activity, the system may prompt the patient to indicate whether they did it/took it today or not, and in specific cases probes for a follow-up question of why they did not do it (e.g., "I did not take this medication because I need a refill", or "I did not exercise today because I didn't feel well enough.").

What the patient did today is captured in the context of their medical condition, their care plan, and "how they feel" and can provide clinicians and patients valuable insights for discussion. For example, a doctor and patient can have a detailed discussion about how a particular medication affects how the patient feels which can lead to optimizing dosage or choosing the right medication for a specific patient. The present system also improves medication compliance and healthy choices when the patient is able to see the connection between what they do and how they feel.

It should be appreciated by those skilled in the art that the foregoing description provides a powerful tool for processing patient feedback for determining complications and/or conditions that may be acted upon by a caregiver. While at least one exemplary embodiment has been presented in the foregoing detailed description, it should be appreciated that a vast number of variations exist. It should also be appreciated that the example embodiment or embodiments described herein are not intended to limit the scope, applicability, or configuration of the invention in any way. Rather, the foregoing detailed description will provide those skilled in the art with a convenient and edifying road map for implementing the described embodiment or embodiments. It should be understood that various changes can be made in the function and arrangement of elements without departing from the scope of the invention and the legal equivalents thereof.

What is claimed is:

1. A system for early detection of an adverse health trend during a monitoring period for a health event, the system comprising:
 a patient device comprising:
  a storage;
  a processor, operatively coupled to the storage;
  an input, operatively coupled to the processor;
  a communication interface, operatively coupled to the processor; and
  a display, operatively coupled to the processor,
   wherein the processor is configured to process patient feedback data received from the input, provide a keyword cloud to the display, and receive selection of one or more keywords in the keyword cloud via the input, the keyword cloud comprising a plurality of at least one of symptoms, complications, medication side effects, phase of care, and patient conditions each of which are based on the health event,
   wherein the keyword cloud is structured by the processor for display in accordance with previous selection of one or more previously displayed keywords stored in the storage and inputted during a monitoring period for the health event defined as a period between a first date in which monitoring for the health event begins and a second date in which monitoring for the health event ends,
   wherein the feedback data and the received selection of the one or more keywords are stored in the storage and/or transmitted via the communication interface for structuring subsequently displayed keyword clouds, and
   wherein the received selection of the keyword is transmitted via the communication interface; and
 a server in data communication with the patient device,
  wherein the server includes a computer program for a health care provider portal embedded in a computer readable medium comprising computer executable instructions for execution by a processor, the computer program comprising:
   instructions to receive in real time the selection of the one or more keywords inputted on the patient device and transmitted by the communication interface;
   instructions to determine a weight from the selection of the one or more keywords in the keyword cloud based on a predicted correlation between the selection and a potential adverse health condition;
   instructions to identify a particular potential adverse health condition from a plurality of potential adverse health conditions based on the weight determined from the selection of the one or more keywords in the keyword cloud exceeding a threshold weight associated with the particular potential adverse health condition;
   instructions to output in real-time, via a second display operatively connected to the server, an alert in response to a determination the threshold weight associated with the particular potential adverse health condition has been exceeded, wherein the alert includes the one or more selected keywords associated with the particular potential adverse health condition and the threshold to a healthcare provider utilizing the healthcare provider portal;
   instructions to receive from a healthcare provider a customized care plan for the patient from a second input operatively connected to the server in response to the alert; and
   instructions to transmit the customized care plan to the patient device, wherein the transmitted customized care plan is displayed to the patient via the patient device display.

2. The system of claim 1, wherein the processor is configured to modify an appearance of at least one keyword in the keyword cloud in response to a selection of the at least one keyword via the input.

3. The system of claim 1, wherein the processor is configured to modify an appearance of at least one keyword in the keyword cloud in response to a previous selection of the at least one keyword via the input.

4. The system of claim 2, wherein the processor is configured to:
 modify an appearance of at least one other keyword in the keyword cloud in response to a previous selection of the at least one other keyword via the input; and
 cluster the at least one keyword and at least one other keyword in the keyword cloud.

5. The system of claim 1, wherein the processor is configured to modify the structured keyword cloud in accordance with a progression of at least one of the symptoms, the complications, the medication side effects, the phase of care, and the patient conditions.

6. The system of claim 1, wherein the processor is configured to replace at least one of the keywords in the keyword cloud with at least one replacement keyword based on a previous non-selection of the at least one keyword.

7. The system of claim 1, wherein the processor is configured to replace at least one of the keywords in the keyword cloud with at least one replacement keyword based on a previous selection of another keyword.

8. One or more non-transitory, computer-readable storage media comprising a plurality of instructions that in response to being executed cause a computing device to:
 receive real time updates of patient feedback data transmitted by a patient device from selection of one or more keywords from a keyword cloud comprising a plurality of at least one of symptoms, complications, medication side effects, phase of care, and patient conditions each of which are based on a health event, wherein the keyword cloud is structured in accordance with previous selection of one or more previously displayed keywords inputted on the patient device during a monitoring period for the health event defined as a period between a first date in which monitoring for the health event begins and a second date in which monitoring for the health event ends inputted on the patient device for structuring subsequently displayed keyword clouds;
 determine a weight from the selection of the one or more keywords in the keyword cloud based on a predicted correlation between the selection and a potential adverse health condition;
 identify a particular potential adverse health condition from a plurality of potential adverse health conditions based on the weight determined from the selection of the one or more keywords in the keyword cloud exceeding a threshold weight associated with the particular potential adverse health condition;
 output, in real-time, to a healthcare provider portal accessible via a server an alert in response to a determination the threshold weight associated with the particular potential adverse health condition has been exceeded, wherein the alert includes the one or more selected keywords associated with the particular potential adverse health condition and the threshold;

receive, via the healthcare provider portal, a customized care plan for the patient in response to the alert; and transmit the customized care plan to the patient device.

9. The one or more non-transitory, computer-readable storage media of claim 8, further comprising instructions to modify an appearance of at least one keyword in the keyword cloud in response to a selection of the at least one keyword via the input.

10. The one or more non-transitory, computer-readable storage media of claim 8, further comprising instructions to modify an appearance of at least one keyword in the keyword cloud in response to a previous selection of the at least one keyword via the input.

11. The one or more non-transitory, computer-readable storage media of claim 10, further comprising instructions to:

modify an appearance of at least one other keyword in the keyword cloud in response to a previous selection of the at least one other keyword via the input; and cluster the at least one keyword and at least one other keyword in the keyword cloud.

12. The one or more non-transitory, computer-readable storage media of claim 8, further comprising instructions to modify the structured keyword cloud in accordance with a progression of at least one of the symptoms, the complications, the medication side effects, the phase of care, and the patient conditions.

13. The one or more non-transitory, computer-readable storage media of claim 8, further comprising instructions to replace at least one of the keywords in the keyword cloud with at least one replacement keyword based on a previous non-selection of the at least one keyword.

14. The one or more non-transitory, computer-readable storage media of claim 8, further comprising instructions to replace at least one of the keywords in the keyword cloud with at least one replacement keyword based on a previous selection of another keyword.

15. A method for early detection of an adverse health trend during a monitoring period for a health event, the method comprising the steps of:

presenting, via a processor, a keyword cloud on a display of a patient device, wherein the keyword cloud comprises a plurality of at least one of symptoms, complications, medication side effects, phase of care, and patient conditions each of which are based on the health event, wherein the keyword cloud is structured in accordance with previous selection of one or more previously displayed keywords inputted on the patient device during a monitoring period for the health event defined as a period between a first date in which monitoring for the health event begins and a second date in which monitoring for the health event ends;

receiving in real time, by a server, the selection of one or more keywords in the keyword cloud from the patient device;

determining, by a server, a weight from the selection of the one or more keywords in the keyword cloud based on a predicted correlation between the selection and a potential adverse health condition;

identifying, by a server, a particular potential adverse health condition from a plurality of potential adverse health conditions based on the weight determined from the selection of the one or more keywords in the keyword cloud exceeding a threshold weight associated with the particular potential adverse health condition;

outputting in real-time, via a second display operatively connected to the server, an alert in response to a determination the threshold weight associated with the particular potential adverse health condition has been exceeded, wherein the alert includes the one or more selected keywords associated with the particular potential adverse health condition and the threshold to a healthcare provider utilizing the healthcare provider portal;

receiving from a healthcare provider a customized care plan for the patient from a second input operatively connected to the server in response to the alert; and transmitting the customized care plan to the patient device, wherein the transmitted customized care plan is displayed to the patient via the patient device display.

16. The method of claim 15, further comprising the step of modifying an appearance of at least one keyword in the keyword cloud via the processor in response to a selection of the at least one keyword via the input.

17. The method of claim 15, further comprising the step of modifying an appearance of at least one keyword in the keyword cloud via the processor in response to a previous selection of the at least one keyword via the input.

18. The method of claim 17, further comprising the steps of:

modifying an appearance of at least one other keyword in the keyword cloud in response to a previous selection of the at least one other keyword via the input; and clustering the at least one keyword and at least one other keyword in the keyword cloud.

19. The method of claim 15, further comprising the step of modifying the structured keyword cloud via the processor in accordance with a progression of at least one of the symptoms, the complications, the medication side effects, the phase of care, and the patient conditions.

20. The method of claim 15, further comprising the step of replacing at least one of the keywords in the keyword cloud with at least one replacement keyword via the processor based on a previous non-selection of the at least one keyword.

21. The method of claim 15, further comprising the step of replacing at least one of the keywords in the keyword cloud via the processor with at least one replacement keyword based on a previous selection of another keyword.

* * * * *